United States Patent [19]

Miller et al.

[11] Patent Number: 5,190,550
[45] Date of Patent: Mar. 2, 1993

[54] LOCKING SURGICAL TOOL HANDLE SYSTEM

[75] Inventors: Gary J. Miller; Matthew Lyons, both of Gainesville, Fla.

[73] Assignee: Exactech, Inc., Gainesville, Fla.

[21] Appl. No.: 881,688

[22] Filed: May 12, 1992

Related U.S. Application Data

[63] Continuation-in-part of Ser. No. 561,801, Aug. 2, 1990.

[51] Int. Cl.[5] .......................... A61B 17/00; A61F 2/32
[52] U.S. Cl. .......................................... 606/85; 606/99
[58] Field of Search .................. 606/53, 79, 84, 85, 606/176, 80, 91, 104, 99, 100; 411/473

[56] References Cited

U.S. PATENT DOCUMENTS

| | | |
|---|---|---|
| 2,329,398 | 9/1943 | Duffy ............................ 606/104 |
| 3,604,487 | 9/1971 | Gilbert .......................... 606/104 |
| 4,263,903 | 4/1981 | Griggs ........................... 411/473 |
| 4,306,550 | 12/1981 | Forte ............................. 606/85 |
| 4,531,517 | 7/1985 | Forte ............................. 606/99 |
| 4,583,270 | 4/1986 | Kenna ........................... 606/85 |
| 4,587,964 | 5/1986 | Walker .......................... 606/85 |
| 4,601,289 | 7/1986 | Chiarizzio ..................... 606/85 |
| 4,765,328 | 8/1988 | Keller ............................ 623/18 |
| 4,921,493 | 5/1990 | Webb ............................. 606/85 |
| 4,990,149 | 2/1991 | Fallin ............................ 606/85 |

Primary Examiner—Michael A. Brown
Attorney, Agent, or Firm—Spensley Horn Jubas & Lubitz

[57] ABSTRACT

A locking surgical tool handle system. The invention includes a surgical tool handle that has an elongated body portion with a pistol-type grip. The front end of the handle body has a tool retaining structure comprising a contoured engagement face and a moveable tension bar with an engagement end. Projections on the engagement end of the tension bar fit within a receiving channel of a surgical tool, such as a broach or rasp. A locking mechanism is provided within the handle body, and is implemented with pivotable links attached to the tension bar. The locking mechanism has an unlocked position in which the engagement end of the tension bar is spaced away from the engagement face of the handle body, and an over-center locked position in which the engagement end of the tension bar is retracted toward the handle body. When the tool handle is placed in its locked position, the engagement end of the tension bar pulls an attached tool into tight contact with the engagement face of the handle body.

8 Claims, 4 Drawing Sheets

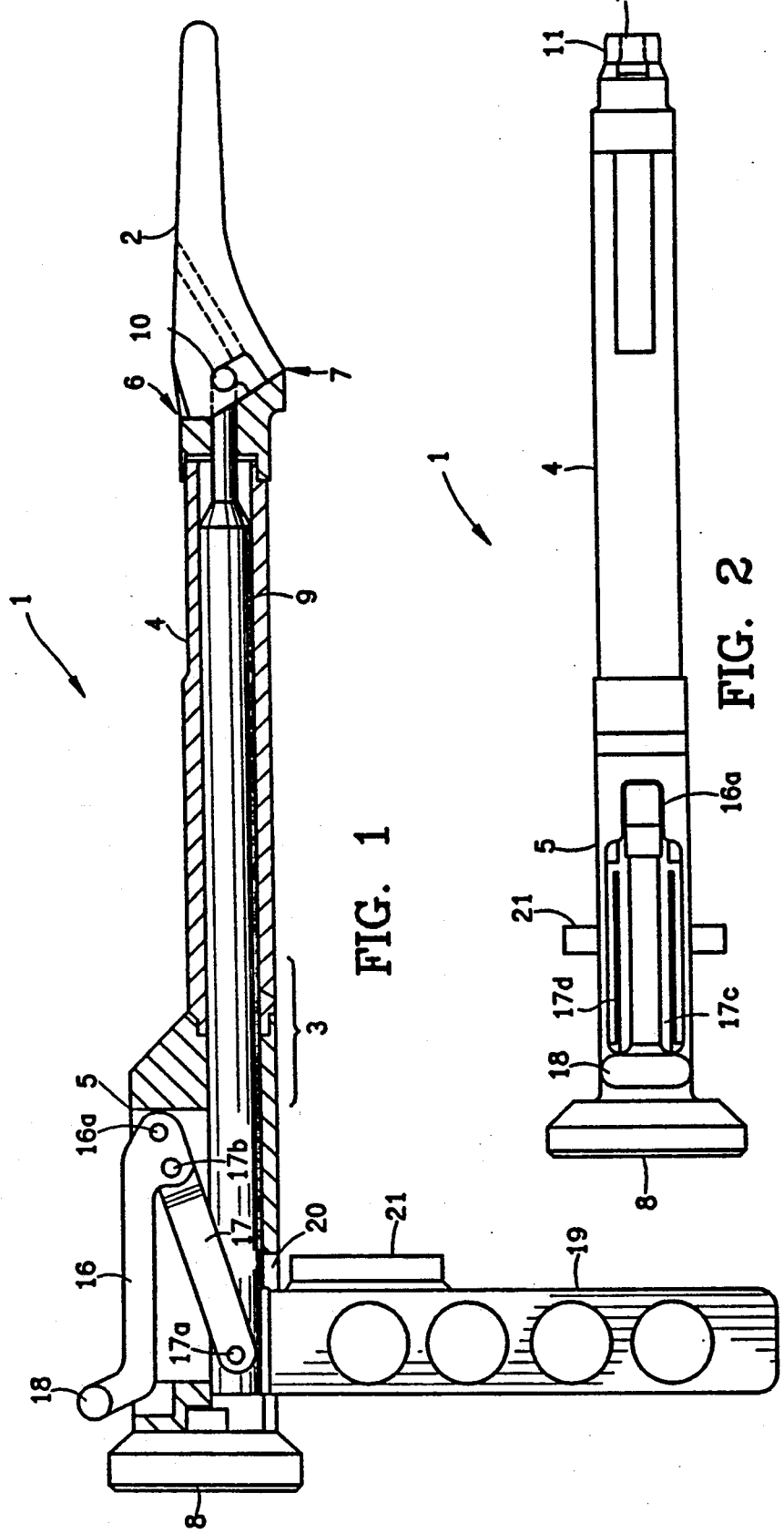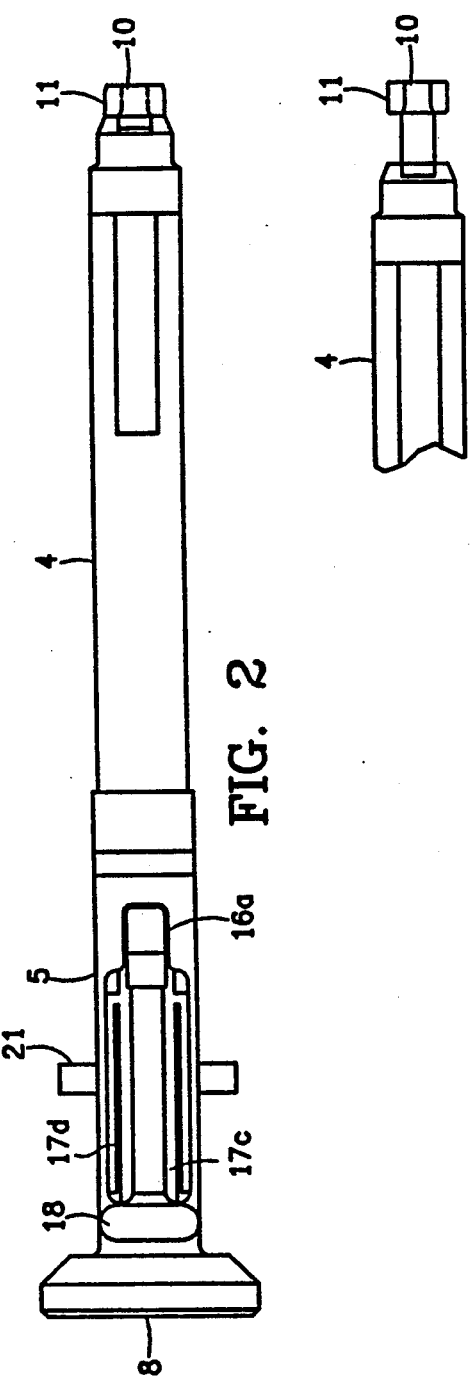

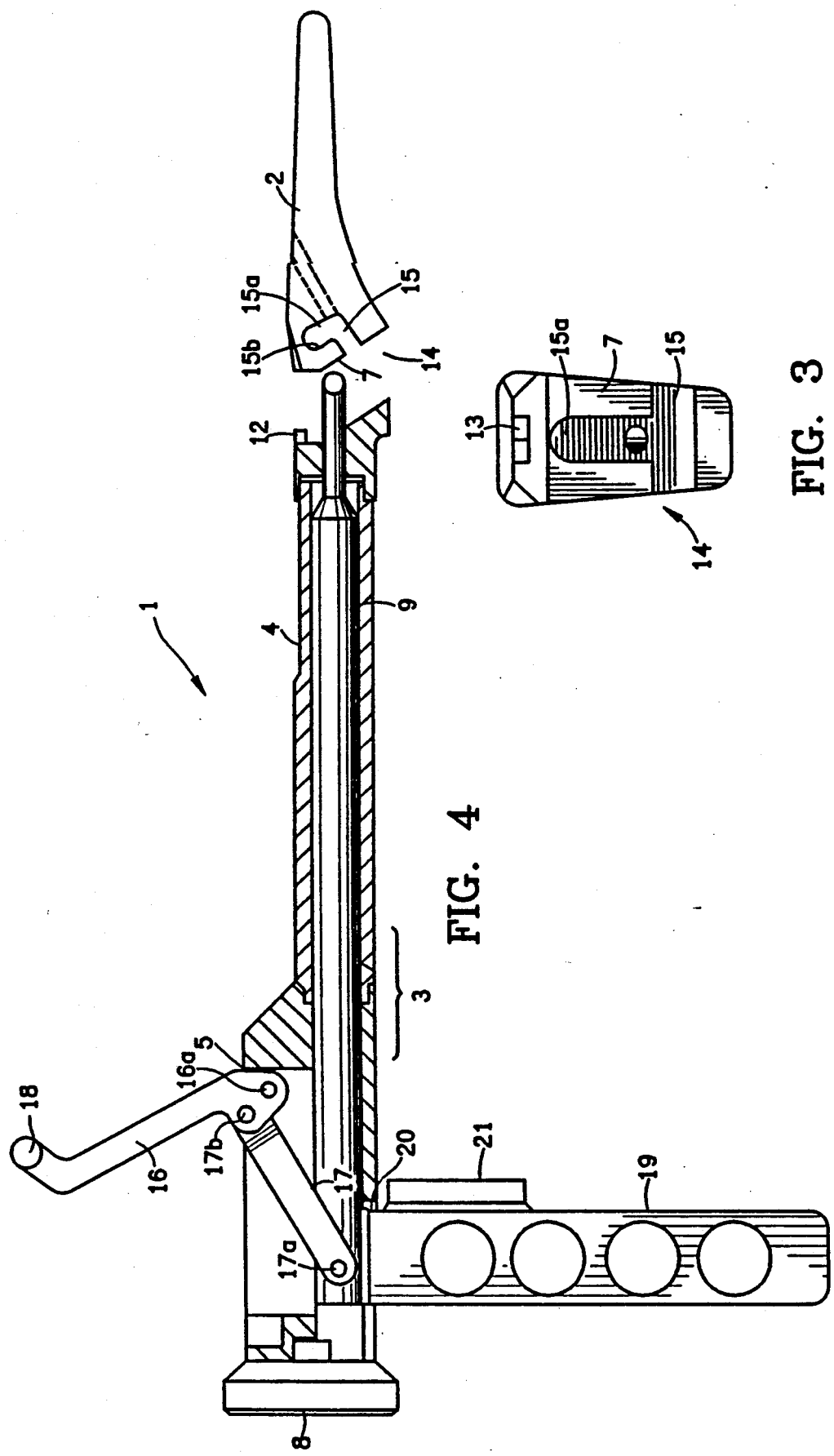

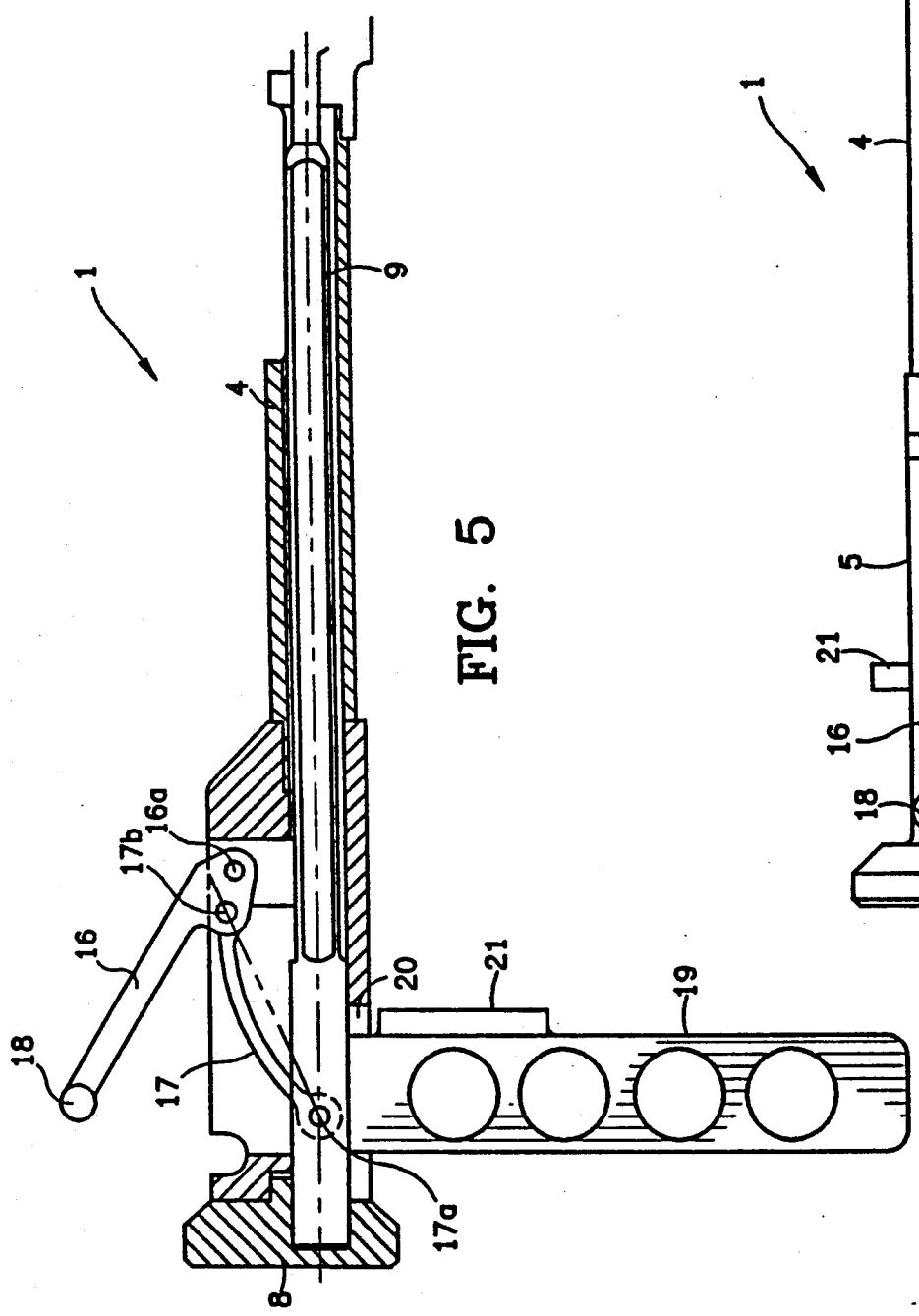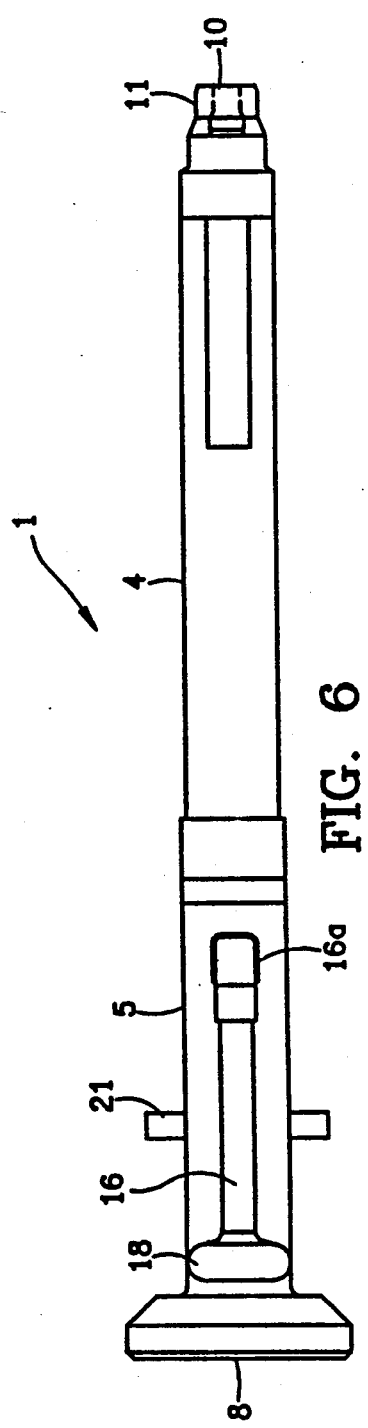

LOCKING SURGICAL TOOL HANDLE SYSTEM

This application is a continuation-in-part of copending U.S. application Ser. No. 07/561,801 filed Aug. 2, 1990.

BACKGROUND OF THE INVENTION

1. Field of the Invention

This invention relates to surgical instruments, and more particularly to a locking surgical tool handle system.

2. Related Art

The use of prosthetic implants to replace the natural joints of a body, either as a result of disease or injury to the natural joint, is becoming more and more commonplace. For example, in the replacement of a hip joint, it is very often necessary to replace the natural femoral head with a prosthetic stem fixed within the femur and provide an accurately located and securely held prosthetic head in place of the natural femoral head. The prosthetic stem may be of a press-fit type, or a cemented type.

The procedure for implanting a prosthetic stem includes the use of a broach or rasp, usually as the last step in preparing the proximal femoral shaft for the reception of the prosthetic stem. The purpose of the broach or rasp is to provide contouring of the proximal femoral shaft to the gross geometry of the prosthetic stem, thereby assuring accurate location and good fit. The configuration of the broach or rasp is made to emulate that of the prosthetic stem (and its cement mantle, when used) to enable the attainment of the desired stem shape.

In order to facilitate utilization of such a broach or rasp, it has been suggested that the handle of the instrument be selectively detachable from the instrument tool so that the location of the tool within the femoral shaft can be gauged precisely and used as a means of determining the subsequent location of the prosthetic stem. Further, if the handle is detachable, the tool may be used for location of a trial neck attachment to assure that the length of the reconstructed prosthesis is accurate, and for milling of the femoral calcar (through an opening in the tool) to assure that the bone surface is flat and in line with the face of the tool.

A number of handles for use with releasable broaches or rasps have been proposed in the past. Examples are given in U.S. Pat. Nos. 4,306,550; 4,583,270; 4,587,964; 4,601,289; and 4,765,328. However, these existing handles exhibit a number of problems. Several fail to achieve a tight fit between the tool and handle. A tight fit is necessary to permit good control of the tool during a surgical procedure. Many of the existing handles suffer a high rate of failure between the attachment peg or other interfacial locking component between the handle and tool. A few of the existing designs simply cannot withstand repeated impacts necessary during insertion and removal of a broach or rasp. Lastly, a number of the designs are nonergonomic, which makes use difficult during a surgical procedure.

It is therefore desirable to provide an ergonomic handle that attaches to cutting tools used during surgery, and in particular, that attaches to rasps and broaches used to fashion the intramedullary canal of the femur during a hip replacement procedure. It is also desirable to provide a design that incorporates proper balance, rigid construction, secure locking of a tool to the handle, quick release to facilitate usage during surgery, and rugged design that survives through repeated impacts during insertion and removal of a tool in surgery.

The present invention provides a locking surgical tool handle that meets these goals.

SUMMARY OF THE INVENTION

The invention includes a surgical tool handle that has an elongated body portion with a pistol-type grip. The front end of the handle body has a tool retaining structure comprising a contoured engagement face and a movable tension bar with an engagement end. Projections on the engagement end of the tension bar fit within a receiving channel of a surgical tool, such as a broach or rasp.

A locking mechanism is provided within the handle body, and is implemented with pivotable links attached to the tension bar. The locking mechanism has an unlocked position in which the engagement end of the tension bar is spaced away from the engagement face of the handle body, and an over-center locked position in which the engagement end of the tension bar is retracted toward the handle body. When the tool handle is placed in its locked position, the engagement end of the tension bar pulls an attached tool into tight contact with the engagement face of the handle body.

The present invention provides a surgical tool coupling system which enables effective selective attachment and detachment of a surgical tool from the tool handle. The design of the preferred embodiment exhibits strength and rigidity in the connection between a tool and a handle for accuracy and precision in the use of the tool; ease of attachment or detachment of the tool, for facilitating the use of the detachable handle feature under the conditions encountered during a surgical procedure, and, in particular, enabling quick and reliable attachment or detachment under operating room conditions; simplicity in the number and configuration of the component parts of the tool handle, enabling ease of maintenance as well as use; compliance with all the requirements for surgical instruments insofar as materials and construction necessary to serve in a surgical environment; and a rugged construction for reliable service over an extended service life.

The details of the preferred embodiment of the present invention are set forth in the accompanying drawings and the description below. Once the details of the invention are known, numerous additional innovations and changes will become obvious to one skilled in the art.

DESCRIPTION OF THE DRAWINGS

FIG. 1 is a cross-sectional side view of one embodiment of the surgical tool handle, shown in its locked position with a tool attached.

FIG. 2 is a top view of the embodiment of the surgical tool handle of FIG. 1, shown in its locked position.

FIG. 2a is a top view of the front end of the surgical tool handle, shown in its unlocked position.

FIG. 3 is an end view of a tool used in conjunction with the surgical tool handle.

FIG. 4 is a cross-sectional side view of the embodiment of the surgical tool handle of FIG. 1, shown in its unlocked position, juxtaposed to the engagement end of a tool.

FIG. 5 is a cross-sectional side view of another embodiment of the surgical tool handle.

FIG. 6 is a top view of the embodiment of the surgical tool handle of FIG. 5.

Like reference numbers and designations in the drawings refer to like elements.

DETAILED DESCRIPTION OF THE INVENTION

Figure 7:
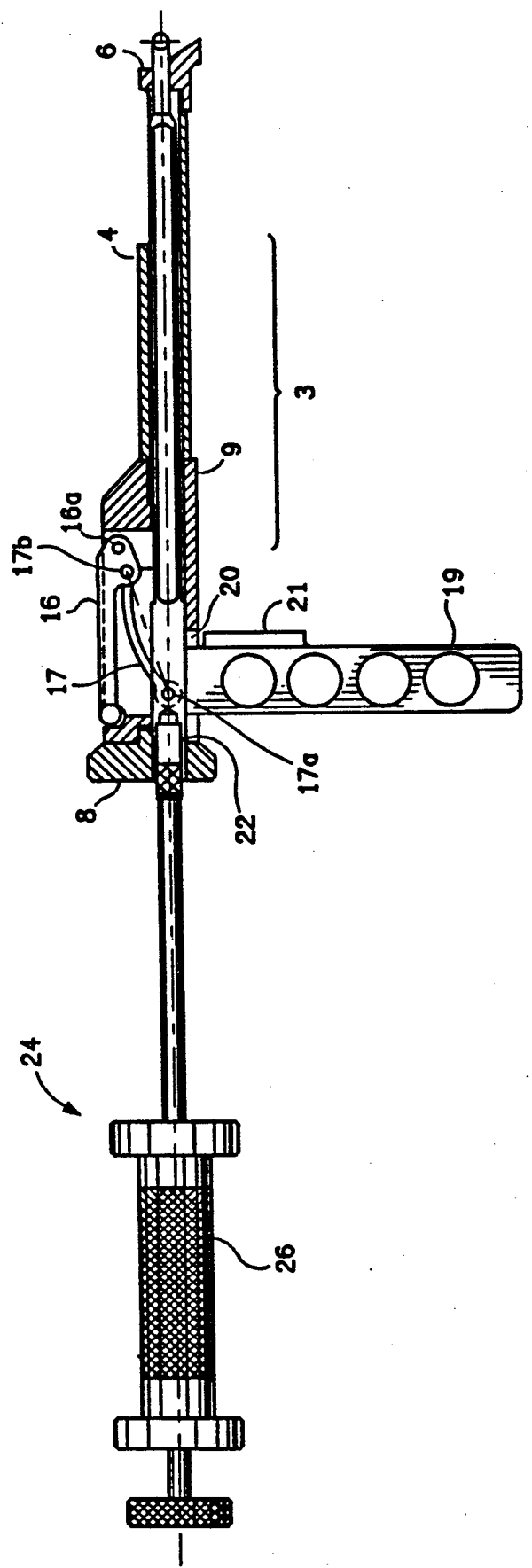
FIG. 7 is a cross-sectional side view of yet another embodiment of the surgical tool handle including a hammer component.

Throughout this description, the preferred embodiment and examples shown should be considered as exemplars, rather than limitations on the structure of the present invention.

FIG. 1 shows a cross-sectional side view of a first embodiment of the inventive surgical tool handle 1 with a tool 2 attached. The tool handle 1 includes an elongated handle body 3 having a hollow front barrel 4 and a rear lock housing 5. The barrel 4 may be attached to the lock housing 5 by means of a threaded coupling, or the two elements may be constructed as a unitary structure. The front end of the barrel 4 is affixed to an engagement face 6, which is contoured to fit closely to a corresponding mating face 7 of the tool 2.

The handle body 3 has an insertion striking plate 8 on one end, to receive impacts from a surgical mallet and transmit the impact forces down the axis of the handle body 3 to the attached tool 2. The design of the present invention permits the transmittal of impacts on the insertion strike plate 8 to be directly transmitted to the tool 2 through the contacting engagement face 6 and tool mating face 7 without being transmitted through the fastening structure and thus without jeopardizing the locking mechanism of the tool handle.

Situated within the handle body 3 is a tension bar 9, which is slidable within the interior of the handle body 3. An engagement end 10 of the tension bar 9 projects through the engagement face 6 of the barrel 4. The engagement end 10 of the tension bar 9 is formed with at least one engagement projection 11 (see FIG. 2a) projecting approximately perpendicular to the longitudinal axis of the tension bar 9. In the preferred embodiment, the engagement projections 11 are formed from dual bars extending perpendicular to the tension bar 9, causing the engagement end 10 of the tension bar 9 to have a "T"-shaped configuration.

The engagement face 6 of the preferred embodiment of the invention may include a boss 12 at one edge of the engagement face 6 (see FIG. 4). The boss 12 mates with a matching indentation 13 in the tool 2 (see FIG. 3), and serves as a stop that prevents sliding movement and inhibits rotation of the tool 2 with respect to the engagement face 6, once the tool 2 is pulled into locking engagement by retraction of the tension bar 9.

As noted above, the tool 2 has a mating face 7 configured to closely fit the engagement face 6 of the handle body 3. Formed into the attachment end 14 of the tool 2 is a channel 15 configured to be engaged by the engagement projections 11 of the tension bar 9 (see also FIG. 3). In the preferred embodiment, the channel 15 is "L"-shaped when viewed from the side, such that the "T"-shaped engagement projections 11 enter into the channel opening and are then positioned up into a channel recess 15a, which may include a detent 15b.

The other end of the tension bar 9 is coupled to a locking mechanism which in the first embodiment comprises an upper link 16 and a lower link 17. The upper link 16 is pivotally coupled to the lock housing 5 at a housing pivot 16a. The upper link 16 also has a lock handle 18 for ease of use. The lower link 17 is pivotally coupled to the tension bar 9 at a tension bar pivot 17a, and to the upper link 16 at a link pivot 17b. As shown, for example, in FIG. 2, lower link 17 of the first embodiment comprises two straight elements 17c and 17d attached bilaterally to tension bar 9 by pivots 17a.

In a second embodiment of the invention shown in FIGS. 5 and 6, link 17 comprises a single element 17 centrally attached to tension bar 9 by a pivot 17a. While the single link element 17 shown in FIGS. 4 and 5 is curved, other link configurations may be utilized, e.g., straight or "S" shaped links.

The tool handle 1 also includes a hand grip 19 for holding the tool handle 1. The grip 19 is preferably mounted at a comfortable angle with respect to the handle body 3. In the preferred embodiment, the angle is approximately 90°, but other angles may be chosen if desired. In the preferred embodiment, the grip 19 is directly attached to the tension bar 9. An opening 20 in the lock housing 5 permits the grip 19 to slide with the tension bar 9 as the tension bar 9 moves from its unlocked position to its locked position.

A removal striking plate 21 is mounted on the grip 19 such that the face of the striking plate 21 is perpendicular to the handle body 3. The removal striking plate 21 serves as a striking surface aligned along the axis of the handle body 3, which permits transmittal of striking impacts from a surgical mallet parallel to that axis. Because of the direct connection between the grip 19 and the tension bar 9, impacts made on the removal striking plate 21 are directly imparted to the tension bar 9, and thus directly to an attached tool 2 through the engagement end 10. This permits a surgeon to remove a tool from a femur, for example, in a straight line fashion, rather than at an angle to the bone.

FIG. 7 illustrates another embodiment of the invention wherein striking plate 8 is designed to accommodate a striking tool. Specifically, in this embodiment, striking plate 8 is provided with an opening 22 positioned in line with the tension bar 9. A striking tool such as the illustrated slap hammer 24 is placed within the opening 22. When the slide weight 26 of the hammer 24 is moved down it impacts the striking plate 8 to drive the tension bar 9. When the slide weight 26 is driven up, on the other hand, it creates a direct extraction force on the tension bar. This embodiment of the surgical tool handle is particularly operating room friendly.

As shown in FIGS. 1 and 4 or FIGS. 5 and 6, the locking handle 18 has two positions. In the locked position shown in FIG. 1, the link pivot 17b is in-line with the housing pivot 16a and the tension bar pivot 17a. This position of the link pivot 17b maximizes the distance between the housing pivot 16a and the tension bar pivot 17a, and creates the greatest effective length for the lower link 17. If the link pivot 17b is moved off of the line between the housing pivot 16a and the tension bar pivot 17a, the effective length of the lower link 17 is decreased.

When a tool 2 is situated such that the engagement projections 11 are within the detent 15b of the channel recess 15a of a tool 2, moving the lock handle 18 into its locked position increases the effective length of the lower link 17. The tension bar pivot 17a end of the lower link 17 is forced towards the rear of the tool handle 1, pulling the tension bar 9 backwards into the tool handle 1. The tension bar 9 therefore pulls the tool 2 into tight contact against the engagement face 6 and the boss 12 of the tool handle 1. In the preferred embodiment of the invention, the lock mechanism in its locked position is in a stable, self-retaining "over-center" position. Therefore, the lock handle 18 will not move from its locked position without the application of sufficient force to move the lock handle 18 past its center position.

In the unlocked position shown in FIGS. 4 and 6, the lock handle 18 is raised out from the lock housing 5, pivoting the upper link 16 around the housing pivot 16a. The link pivot 17b end of the lower link 17 is moved off of the line between the housing pivot 16a and the tension bar pivot 17a, thereby decreasing the effective length of the lower link 17. The lower link 17 pulls the tension bar pivot 17a forward toward the front end of the tool handle 1. This change in geometry of the lower link 17 with respect to the upper link 16 pushes the tension bar 9 forward within the barrel 4 of the tool handle 1. The engagement projections 11 of the tension bar 9 are thus moved away from the engagement face 6 of the tool handle 1. The tool 2 may then be disengaged from the engagement projections 11 by moving the engagement projections 11 out of the channel recess 15a and through the opening of the channel 15.

The locking mechanism thus provides a quick and easy means of attaching or detaching a tool 2 from the tool handle 1. The invention is simple in construction, and is preferably completely made of metal (for example, stainless steel) to make sterilization easier in a medical setting.

A number of embodiments of the present invention have been described. Nevertheless, it will be understood that various modifications may be made without departing from the spirit and scope of the invention. For example, the shape of the engagement projections 11 can be changed as desired, and can include a hook-like or disk-shaped projection, so long as the engagement projections 11 can engage a tool 2 such that tension provided by the locked tension bar 9 pulls the tool 2 into tight contact with the engagement face 6. Similarly, the channel 15 of the tool 2 can be formed in various shapes and orientations, so long as the engagement projections 11 can engage the tool 2 securely. Further, the tension bar 9 could be replaced by a flexible tension element, such as a wire cable, since the principal function of the tension bar 9 is to pull a tool 2 tightly against the engagement face 6 of the tool handle 1. Further still, the tool 2 can be of any type, and is not limited to broaches or rasps used for hip replacement surgery.

Accordingly, it is to be understood that the invention is not to be limited by the specific illustrated embodiment, but only by the scope of the appended claims.

We claim:

1. A locking surgical tool handle system, comprising:
   a. a tool having a flanged recess for receiving at least one engagement projection;
   b. a tool handle, including:
      (1) a body having an engagement end and a hollow shaft disposed within the body;
      (2) a tension element disposed within the shaft of the body, the tension element extending out from the engagement end of the body and having at least one engagement projection for engaging the recess of a tool;
      (3) locking means, coupled to the tension element, for pulling the tension element into a locked position within the body when at least one engagement projection is disposed within the recess of a tool the locking means comprising (a) a first link centrally coupled to the tension element by a tension element pivot, and (b) a second link coupled to the first link by a link pivot, and to the body by a body pivot, and having a handle end;
   whereby the tool is held to the engagement end of the tool handle by the application of tension to the tool by the tension element when the locking means is in its locked position.

2. The locking surgical tool handle of claim 1, wherein the first link means of the locking means comprises two link elements coupled bilaterally to the tension element.

3. The locking surgical tool handle of claim 1, wherein the first link has a straight shape.

4. The locking surgical tool handle of claim 1, wherein the first link has a curved shape.

5. The locking surgical tool handle of claim 1, wherein the first link has an "S" shape.

6. The locking surgical tool handle of claim 1, wherein the body of the tool handle further includes a striking end located opposite of the engagement end.

7. The locking surgical tool handle of claim 6, wherein the striking end of the body comprises means for engaging a striking tool.

8. The locking surgical tool handle of claim 7, wherein the striking tool comprises a slap hammer and wherein the means for engaging comprises an opening provided in the striking end of the body in line with the hollow shaft.

* * * * *